United States Patent [19]

Martin et al.

[11] Patent Number: 4,999,358
[45] Date of Patent: Mar. 12, 1991

[54] (1,2,3,4-TETRAHYDRO-9-ACRIDINIMINO)-CYCLOHEXANE CARBOXYLIC ACID AND RELATED COMPOUNDS

[75] Inventors: Lawrence L. Martin, Lebanon; Joseph F. Payack, Somerset; Helen H. Ong, Whippany, all of N.J.

[73] Assignee: Hoechst-Roussel Pharmaceuticals Inc., Somerville, N.J.

[21] Appl. No.: 371,228

[22] Filed: Jun. 26, 1989

[51] Int. Cl.$^5$ .................. C07D 219/10; A61K 31/47
[52] U.S. Cl. ................................ 514/297; 546/105; 546/106
[58] Field of Search ............... 546/105, 106; 514/297

[56] References Cited

U.S. PATENT DOCUMENTS 4,851,536  7/1989  Skotnicki et al. ............... 546/106

FOREIGN PATENT DOCUMENTS 0268871  6/1988  European Pat. Off.

Primary Examiner—Nicholas S. Rizzo
Attorney, Agent, or Firm—Tatsuya Ikeda

[57] ABSTRACT

There are described compounds of the formula,

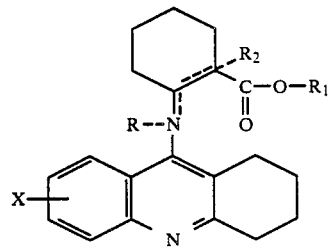

where
X is hydrogen, loweralkyl, loweralkoxy or halogen;
R when present is hydrogen, loweralkyl or arylloweralkyl;
$R_1$ is hydrogen, loweralkyl or arylloweralkyl; and
$R_2$ when present is hydrogen or loweralkyl;

which compounds are useful for alleviating various memory dysfunctions characterized by a decreased cholinergic function such Alzheimer's disease.

20 Claims, No Drawings

(1,2,3,4-TETRAHYDRO-9-ACRIDINIMINO)CYCLOHEXANE CARBOXYLIC ACID AND RELATED COMPOUNDS

The present invention relates to compounds of the formula

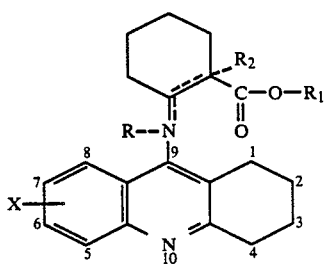

where
X is hydrogen, loweralkyl, loweralkoxy or halogen;
R when present is hydrogen, loweralkyl or arylloweralkyl;
$R_1$ is hydrogen, loweralkyl or arylloweralkyl; and
$R_2$ when present is hydrogen or loweralkyl;
which compounds are useful for treating various memory dysfunctions characterized by a decreased cholinergic function such Alzheimer's disease.

Throughout the specification and appended claims, a given chemical formula or name shall encompass all stereo, optical, tautomeric and geometrical isomers thereof where such isomers exist.

The dotted lines present in Formula I signify the fact that when $R_2$ is present, R is absent and the linkage between the pendant amino nitrogen and the cyclohexane ring is a double bond; and that when $R_2$ is absent, R is present and the linkage between the pendant amino nitrogen and the cyclohexene ring is a single bond. Thus, Formula I encompasses Formulas Ia and Ib depicted below.

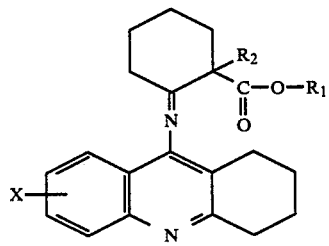

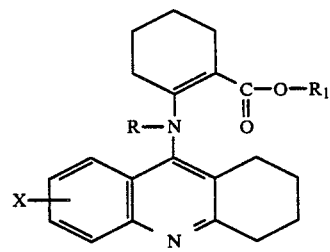

Also included within the scope of this invention as having the utility mentioned above are novel compounds having Formula II depicted below.

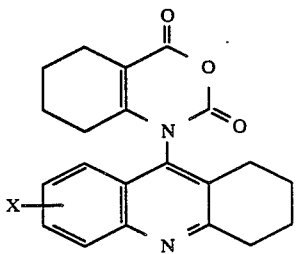

The following general rules of terminology shall apply throughout the specification and the appended claims.

Unless otherwise stated or indicated, the term loweralkyl denotes a straight or branched alkyl group having from 1 to 6 carbon atoms. Examples of said loweralkyl include methyl, ethyl, n-propyl, iso-propyl, sec-butyl and straight-and branched-chain pentyl and hexyl.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term halogen shall means fluorine, chlorine, bromine or iodine.

Unless otherwise stated or indicated, the term aryl shall means a phenyl group optionally substituted with a loweralkyl, loweralkoxy or halogen group.

The compounds of Formula I, II or III of this invention can be synthesized by following or combining one or more of the synthetic steps described below. Throughout the description of the synthetic steps, the definitions of X, R, $R_1$ and $R_2$ are as given above unless otherwise stated or indicated, and other nomenclatures appearing below shall have the same meanings defined in their respective first appearances unless otherwise stated or indicated.

STEP A

A compound of Formula III is allowed to react with ethyl cyclohexanone-2-carboxylate to afford a compound of Formula IV.

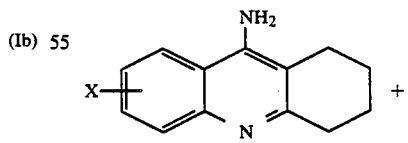

(III)

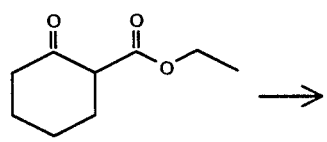

-continued

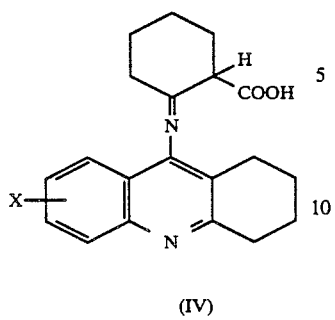

(IV)

This reaction is typically conducted in a suitable solvent such as toluene which permits an azeotropic removal of water at reflux at a temperature of about 80° to 140° C.

STEP B

Compound IV is allowed to react with a loweralkyl bromide of Formula V where $R_3$ is a loweralkyl to afford a compound of Formula VI.

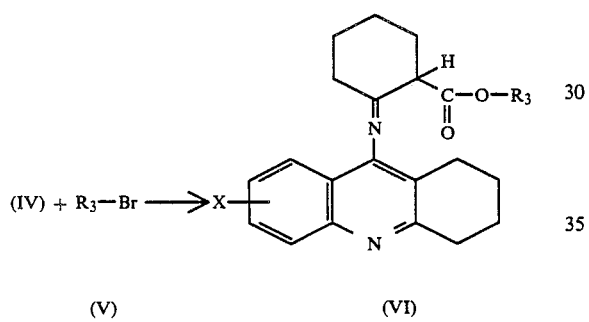

(V)    (VI)

This reaction is typically conducted in the presence of an acid scavenger such as $K_2CO_3$ and a suitable solvent such as N,N-dimethylformamide at a temperature of about 0° to 50° C.

STEP C

Compound IV is allowed to react preferably with about 1 equivalent of a bromide compound of the formula R-Br to afford a compound of Formula VII.

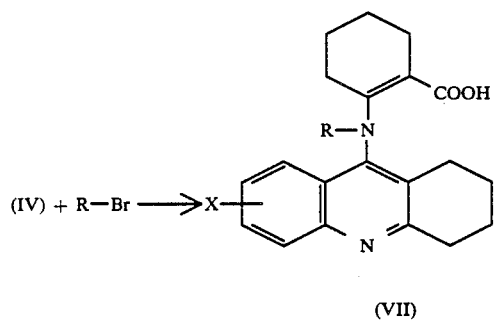

(VII)

This reaction is typically conducted in the presence of an acid scavenger such as $K_2CO_3$ and a suitable solvent such as N,N-dimethylformamide at a temperature of 0° to 50° C.

STEP D

Compound IV is allowed to react preferably with about 2 equivalents (or more) of a bromide compound of the formula R-Br to afford a compound of Formula VIII.

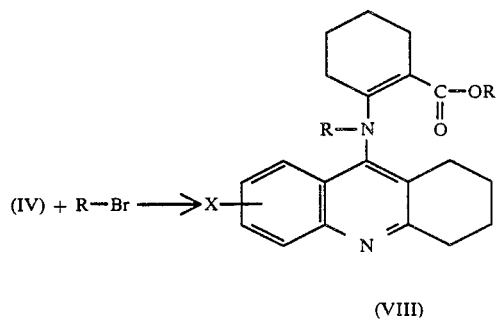

(VIII)

This reaction is conducted in substantially the same manner as in STEP C.

STEP E

Compound IV is allowed to react with a loweralkyl iodide of the formula $R_4$-I where $R_4$ is loweralkyl in the presence of CsF to afford a compound of Formula IX.

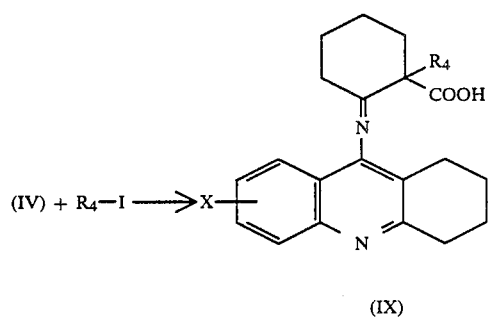

(IX)

This reaction is typically conducted in a suitable medium such as methanol at a temperature of 25° to 100° C.

STEP F

Compound IV is allowed to react with carbonyldiimidazole to afford Compound II.

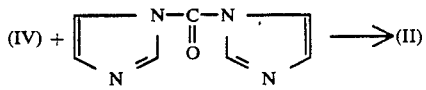

This reaction is typically conducted in a suitable solvent such as tetrahydrofuran at a temperature of 0° to 50° C.

Compounds of the present invention having formula I, II or III are useful for the treatment of various memory dysfunctions characterized by a decreased cholinergic function such as Alzheimer's disease.

This utility is demonstrated by the ability of these compounds to restore cholinergically deficient memory in the Dark Avoidance Assay, where they are in general active over a broader dose range than heretofore known compounds, a distinct therapeutic advantage. In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment.

Test results of scopolamine-induced Dark Avoidance Assay for representative compounds of this invention are presented in Table 1 along with that of a reference compound.

TABLE 1

| DARK AVOIDANCE ASSAY | | |
|---|---|---|
|  | Dose (mg/kg of body weight, s.c) | % of Animals with Scopolamine Induced Memory Deficit Reversal |
| 2-(1,2,3,4-Tetrahydro-9-acridinimino)cyclohexanecarboxylic acid | 0.63 | 53% |
| 2-(1,2,3,4-Tetrahydro-9-acridinimino)cyclohexanecarboxylic acid ethyl ester | 0.16 | 29% |
| 2-[N-(Phenylmethyl)-1,2,3,4-tetrahydro-9-acridinamino]cyclohex-1-ene carboxylic acid phenylmethyl ester | 0.63 | 29% |
| 1-Methyl-2-(1,2,3,4-tetrahydroacrinimino)cyclohexane carboxylic acid | 2.5 | 20% |
| (Reference Compound) Physostigmine | 0.31 | 20% |

The above-mentioned utility of the compounds of this invention can also be ascertained by determining the ability of such compounds to inhibit the activity of the enzyme acetylcholinesterase and thereby increase the acetylcholine level in the brain.

CHOLINESTERASE INHIBITION ASSAY

The ability to inhibit acetylcholinesterase was determined by the photometric method of Ellman et al., Biochem. Pharmacol. 7, 88 (1961). Result of a representative compound of this invention is presented in Table 2 below along with those of some reference compounds.

TABLE 2

| ACETYL CHOLINESTERASE INHIBITION | |
|---|---|
| Compound | $IC_{50}$ (molar conc.) |
| 2-(1,2,3,4-Tetrahydro-9-acridinimino)-cyclohexanecarboxylic acid ethyl ester (Reference Compounds) | $1.52 \times 10^{-5}$ |
| 9-Amino-1,2,3,4-tetrahydroacridine | $3.1 \times 10^{-7}$ |
| Physostigmine | $6.0 \times 10^{-9}$ |

Effective quantities of the compounds of the invention may be administered to a patient by any of the various methods, for example, orally as in capsule or tablets, parenterally in the form of sterile solutions or suspensions, and in some cases intravenously in the form of sterile solutions.

The active compounds of the present invention may be orally administered, for example, with an inert diluent or with an edible carrier, or they may be closed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweeting agent such as surcrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

Examples of the compounds of this invention include:
2-(1,2,3,4-tetrahydro-9-acridinimino)cyclohexanecarboxylic acid;
2-(1,2,3,4-tetrahydro-9-acridinimino)cyclohexanecarboxylic acid ethyl ester;

2-(1,2,3,4-tetrahydro-9-acridinimino)cyclohexanecarboxylic acid n-butyl ester;
2-[N-(phenylmethyl)-1,2,3,4-tetrahydro-9-acridinamino]cyclohex-1-ene carboxylic acid;
2-[N-(phenylmethyl)-1,2,3,4-tetrahydro-9-acridinamino]cyclohex-1-ene carboxylic acid phenylmethyl ester;
1-methyl-2-(1,2,3,4-tetrahydroacridinimino)cyclohexane carboxylic acid;
5,6,7,8-tetrahydro-1-(1,2,3,4-tetrahydroacridin-9-yl)-2H-3,1-benzoxazine-2,4(1H)-dione;
2-[N-ethyl-1,2,3,4-tetrahydro-9-acridinamino]cyclohex-1-ene carboxylic acid;
2-[N-ethyl-1,2,3,4-tetrahydro-9-acridinamino]cyclohex-1-ene carboxylic acid ethyl ester;
2-(7-chloro-1,2,3,4-tetrahydro-9-acridinimino)cyclohexanecarboxylic acid;
2-(7-fluoro-1,2,3,4-tetrahydro-9-acridinimino)cyclohexanecarboxylic acid ethyl ester;
2-(7-methyl-1,2,3,4-tetrahydro-9-acridinimino)cyclohexanecarboxylic acid;
2-(7-methoxy-1,2,3,4-tetrahydro-9-acridinimino)cyclohexanecarboxylic acid;
2-(7-methoxy-1,2,3,4-tetrahydro-9-acridinimino)cyclohexanecarboxylic acid methyl ester;
2-(6-fluoro-1,2,3,4-tetrahydro-9-acridinimino)cyclohexanecarboxylic acid;
2-(6-chloro-1,2,3,4-tetrahydro-9-acridinimino)cyclohexanecarboxylic acid ethyl ester;
2-(6-methyl-1,2,3,4-tetrahydro-9-acridinimino)cyclohexanecarboxylic acid; and
2-(6-methoxy-1,2,3,4-tetrahydro-9-acridinimino)cyclohexanecarboxylic acid;

The following examples are presented in order to illustrate this invention.

EXAMPLE 1

2-(1,2,3,4-Tetrahydro-9-acridinimino)cyclohexanecarboxylic acid

A solution prepared from 9-amino-1,2,3,4-tetrahydroacridine (5.0 g), ethyl cyclohexanone-2-carboxylate (25.2 g) and toluene (75 ml) was stirred and heated at reflux with azeotropic removal of water for 12 hours. The resultant crystalline precipitate was filtered, washed with hexane (500 ml) and ether (300 ml), and dried in vacuo at 50° C. to give 2-(1,2,3,4-tetrahydro-9-acridinimino)cyclohexanecarboxylic

| ANALYSIS: | | | |
|---|---|---|---|
| Calculated for $C_{20}H_{22}N_2O_2$ | 74.50% C | 6.88% H | 8.69% N |
| Found | 74.49% C | 6.87% H | 8.69% N |

EXAMPLE 2

2-(1,2,3,4-Tetrahydro-9-acridinimino)cyclohexanecarboxylic acid ethyl ester

To a stirred mixture prepared from 2-(1,2,3,4-tetrahydro-9-acridinimino)cyclohexanecarboxylic acid (10.0 g), anhydrous potassium carbonate (6.43 g) and N,N-dimethylformamide (200 ml) was added at room temperature a solution of ethyl bromide (4.05 g) and N,N-dimethylformamide (50 ml). The mixture was stirred at room temperature overnight and was then filtered and concentrated to yield a gummy solid. The solid was dissolved in dichloromethane (50 ml), filtered and purified by preparative HPLC. The appropriate fractions were combined and concentrated to yield 1.45 g of 2-(1,2,3,4-tetrahydro-9-acridinimino)-cyclohexanecarboxylic acid ethyl ester, m.p. 121.5°–123.5° C.

| ANALYSIS: | | | |
|---|---|---|---|
| Calculated for $C_{22}H_{26}N_2O_2$ | 75.39% C | 7.48% H | 8.00% N |
| Found | 74.97% C | 7.44% H | 7.87% N |

EXAMPLE 3

2-[N-(Phenylmethyl)-1,2,3,4-tetrahydro-9-acridinamino]-cyclohex-1-ene carboxylic acid A mixture prepared from 2-(1,2,3,4-tetrahydro-9-acridinimino)cyclohexane carboxylic acid (1.50 g), potassium carbonate (1.0 g), benzyl bromide (0.80 g) and dimethylformamide (25 ml) was stirred overnight. The solvent was removed, and the residue dissolved in dichloromethane (40 ml), combined with a second batch (prepared in a similar manner) and filtered to removed insolubles. The filtrate was purified by preparative HPLC. The appropriate fractions were combined and concentrated to yield 2.6 g of 2-[N-(phenylmethyl)-1,2,3,4-tetrahydro-9-acridinamino]cyclohex-1-ene carboxylic acid, m.p. 76°–78° C.

| ANALYSIS: | | | |
|---|---|---|---|
| Calculated for $C_{27}H_{28}N_2O_2$ | 78.61% C | 6.84% H | 6.79% N |
| Found | 78.25% C | 6.95% H | 6.57% N |

EXAMPLE 4

2-[N-(Phenylmethyl)-1,2,3,4-tetrahydro-9-acridinamino]-cyclohex-1-ene carboxylic acid phenylmethyl ester A mixture of (1,2,3,4-tetrahydro-9-acridinimino)cyclohexanecarboxylic acid (4.00 g), benzylbromide (4.52 g), potassium carbonate (5.14 g) and N,N-dimethylformamide (75 ml) was stirred at room temperature for four days. The solvent was evaporated in vacuo, and the resulting oil was purified by preparative HPLC. The appropriate fractions were combined and concentrated to yield 1.94 g of the product as a powder.

A second lot, prepared as above, was combined with the powder and recrystallized from ethyl acetate/hexane to afford 2.10 g of 2-[N-(phenylmethyl)-1,2,3,4-tetrahydro-9-acridinamino]cyclohex-1-ene carboxylic acid phenylmethyl ester, m.p. 144°–145° C.

| ANALYSIS: | | | |
|---|---|---|---|
| Calculated for $C_{34}H_{34}N_2O_2$ | 81.24% C | 6.82% H | 5.57% N |
| Found | 81.15% C | 7.02% H | 5.47% N |

EXAMPLE 5

1-Methyl-2-(1,2,3,4-tetrahydroacridinimino)cyclohexane carboxylic acid

A stirred solution of 2-(1,2,3,4-tetrahydroacrinimino)cyclohexane carboxylic acid (3.5 g), iodomethane (1.54 g), cesium fluoride (8.24 g) and methanol (45 ml) was heated just below reflux for 48 hours. The mixture was cooled, 100 ml water was added, and the methanol was evaporated. The aqueous phase was extracted with dichloromethane (2×75 ml), and the combined organic phase was dried ($Na_2SO_4$), filtered and concentrated to 30 ml final volume. This solution was purified by preparative HPLC. Appropriate fractions were combined and concentrated to yield 1.75 g of crystals, m.p. 198°–200° C. This batch was combined with a similarly prepared batch of material, and was carefully rechromatographed as described above, giving 1.60 g of 1-methyl-2-(1,2,3,4-tetrahydroacrdinamine)cyclohexanecarboxylic acid, m.p. 198°–200° C.

| ANALYSIS: | | | |
|---|---|---|---|
| Calculated for $C_{21}H_{24}N_2O_2$ | 74.97% C | 7.19% H | 8.33% N |
| Found | 74.24% C | 7.15% H | 8.18% N |

EXAMPLE 6

5,6,7,8-Tetrahydro-1-(1,2,3,4-tetrahydroacridin-9-yl)-2H-3,1-benzoxazine-2,4(1H)-dione A suspension of 2-(1,2,3,4-tetrahydro-9-acridinimino)cyclohexane carboxylic acid (200 g) in tetrahydrofuran (30 ml) was treated with a solution of carbonyldiimidazole (5.03 g) and tetrahydrofuran (20 ml). The mixture was stirred at room temperature for 1 hour and then the solvent was removed in vacuo to yield 8.7 g of wet, crude product. This product was combined with another lot prepared in a similar manner and the material was purified by preparative HPLC. The appropriate fractions were combined and concentrated to yield 3.95 g of 5,6,7,8-tetrahydro-1-(1,2,3,4-tetrahydroacridin-9-yl)-2H-3,1-benzoxazine-2,4(1H)-dione, m.p. 233.5°–235.5° C. (decomposed).

| ANALYSIS: | | | |
|---|---|---|---|
| Calculated for $C_{21}H_{21}N_2O_3$ | 72.40% C | 5.79% H | 8.04% N |
| Found | 72.34% C | 5.83% H | 7.90% N |

We claim:
1. A compound of the formula

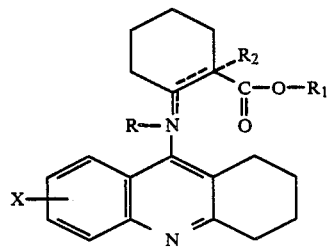

where
X is hydrogen, loweralkyl, loweralkoxy or halogen;
R when present is hydrogen, loweralkyl or arylloweralkyl;
$R_1$ is hydrogen, loweralkyl or arylloweralkyl; and
$R_2$ when present is hydrogen or loweralkyl;
the term aryl in each occurrence independently signifying a phenyl group optionally substituted with a loweralkyl, loweralkoxy or halogen group; or a pharmaceutically acceptable acid addition salt thereof.

2. The compound as defined in claim 1, where X is hydrogen.

3. The compound as defined in claim 1, which is 2-(1,2,3,4-tetrahydro-9-acridinimino)cyclohexanecarboxylic acid.

4. The compound as defined in claim 1, which is 2-(1,2,3,4-tetrahydro-9-acridinimino)cyclohexanecarboxylic acid ethyl ester.

5. The compound as defined in claim 1, which is 2-[N-(phenylmethyl)-1,2,3,4-tetrahydro-9-acridinamino]cyclohex-1-ene carboxylic acid.

6. The compound as defined in claim 1, which is 2-[N-(phenylmethyl)-1,2,3,4-tetrahydro-9-acridinamino]cyclohex-1-ene carboxylic acid phenylmethyl ester.

7. The compound as defined in claim 1, which is 1-methyl-2-(1,2,3,4-tetrahydroacridinimino)cyclohexane carboxylic acid.

8. The compound as defined in claim 1, which is 2-[N-ethyl-1,2,3,4-tetrahydro-9-acridinamino]cyclohex-1-ene carboxylic acid.

9. The compound as defined in claim 1, which is 2-[N-ethyl-1,2,3,4-tetrahydro-9-acridinamino]cyclohex-1-ene carboxylic acid ethyl ester.

10. The compound as defined in claim 1, which is 2-(7-chloro-1,2,3,4-tetrahydro-9-acridinimino)cyclohexanecarboxylic acid.

11. The compound as defined in claim 1, which is 2-(7-fluoro-1,2,3,4-tetrahydro-9-acridinimino)cyclohexanecarboxylic acid ethyl ester.

12. The compound as defined in claim 1, which is 2-(7-methyl-1,2,3,4-tetrahydro-9-acridinimino)cyclohexanecarboxylic acid.

13. The compound as defined in claim 1, which is 2-(7-methoxy-1,2,3,4-tetrahydro-9-acridinimino)cyclohexanecarboxylic acid.

14. The compound as defined in claim 1, which is 2-(7-methoxy-1,2,3,4-tetrahydro-9-acridinimino)cyclohexanecarboxylic acid methyl ester.

15. The compound as defined in claim 1, which is 2-(6-fluoro-1,2,3,4-tetrahydro-9-acridinimino)cyclohexanecarboxylic acid.

16. The compound as defined in claim 1, which is 2-(6-chloro-1,2,3,4-tetrahydro-9-acridinimino)cyclohexanecarboxylic acid ethyl ester.

17. The compound as defined in claim 1, which is 2-(6-methyl-1,2,3,4-tetrahydro-9-acridinimino)cyclohexanecarboxylic acid.

18. The compound as defined in claim 1, which is 2-(6-methoxy-1,2,3,4-tetrahydro-9-acridinimino)cyclohexanecarboxylic acid.

19. A pharmaceutical composition comprising a compound as defined in claim 1 in an amount effective for alleviating a memory dysfunction characterized by a decreased cholinergic function and a suitable carrier therefor.

20. A method of treating a patient in need of relief from a memory dysfunction characterized by a decreased cholinergic function, which comprises administering to such a patient an effective amount of a compound as defined in claim 1.

* * * * *